United States Patent
Ryan et al.

(10) Patent No.: US 6,800,294 B1
(45) Date of Patent: Oct. 5, 2004

(54) ANTIPARASITIC FORMULATION

(75) Inventors: Robert Eugene Ryan, Snetterton (GB); Sandra Morris, Snetterton (GB)

(73) Assignee: Barrier Biotech Limited, Norfolk (GB)

( * ) Notice: Subject to any disclaimer, the term of this patent is extended or adjusted under 35 U.S.C. 154(b) by 0 days.

(21) Appl. No.: 09/926,599

(22) PCT Filed: May 30, 2000

(86) PCT No.: PCT/GB00/02076

§ 371 (c)(1),
(2), (4) Date: Mar. 19, 2002

(87) PCT Pub. No.: WO01/08496

PCT Pub. Date: Feb. 8, 2001

(30) Foreign Application Priority Data

May 27, 1999 (GB) ............................................. 9912443

(51) Int. Cl.⁷ ............................................... A01N 25/02
(52) U.S. Cl. ...................... 424/405; 424/406; 424/522; 424/736; 424/742; 424/747; 424/748; 424/770; 514/316; 514/919
(58) Field of Search ................................. 424/405, 522, 424/742, 736, 747, 748, 770, 406; 514/742, 747, 736, 316

(56) References Cited

U.S. PATENT DOCUMENTS

| | | | | |
|---|---|---|---|---|
| 4,933,371 A | * | 6/1990 | Hink et al. .................. | 514/739 |
| 5,079,000 A | | 1/1992 | Takahashi et al. | |
| 5,194,264 A | * | 3/1993 | Van Tonder ................. | 424/405 |
| 5,403,587 A | | 4/1995 | McCue et al. | |

FOREIGN PATENT DOCUMENTS

| | | | |
|---|---|---|---|
| AU | 51365 | * | 9/1990 |
| CH | 688 787 A | | 3/1998 |
| EP | 0 630 571 A | | 12/1994 |

OTHER PUBLICATIONS

Merck, '68.*
Harvey AU 9051365 Abstract, Sep. 1990.*

* cited by examiner

*Primary Examiner*—Neil S. Levy
(74) *Attorney, Agent, or Firm*—Bacon & Thomas

(57) ABSTRACT

There is disclosed an antiparasitic formulation comprising Eucalyptus oil, Cajeput oil, Lemongrass oil, Clove bud oil, Peppermint oil, Piperonyl and Piperonyl Butoxide. The formulation can be used for treating an animal body or in the manufacture of a medicament for treating ectoparasitic infestation of an animal or for repelling parasites.

11 Claims, No Drawings

ANTIPARASITIC FORMULATION

The present invention is concerned with an antiparasitic formulation and, in particular, with an antiparasitic formulation which can be used to control ectoparasitic infestation and any contagious diseases resulting therefrom.

Ectoparasitic infections of animals such as sheep are widespread. Such parasites include, for example, ticks, mites, lice, keds, head fly and blow fly, amongst others. Ticks contribute to a condition known as tickborne fever which is an infectious disease affecting almost all sheep which graze tick-infected pastures. It is caused by the microorganism *Cytoecetes phogocytophilia,* a rickettsia transmitted via the bite of sheep ticks. Ticks also contribute to tick pyaemia, or "cripples", which is believed to kill or disable in excess of a quarter of a million lambs each year in the UK. Mites on the other hand cause intense irritation to sheep, which react by rubbing against fence posts, or the like. If no fixed objects are available, they rub against each other spreading the disease further- Mites also cause foot scab, a mange infestation of sheep. Blowfly strike, however, is a particularly nasty condition causing untold misery and death to sheep flocks. It is caused by blowfly which feed on decomposing matter containing liquid protein upon which: the blowfly feeds and amongst which it lays its eggs. Any open wound will, attract the flies. Once the larvae hatch, the sheep can be literally eaten alive by successive waves of maggots.

Many antiparasitic formulations are known, for example, as pour-on formulations or as total immersion dips for treating sheep. Plunge dipping is a technique which is generally used to control certain parasitic infestations of sheep, such as skin parasites, because it allows thorough penetration of the fleece and access to the skin by the antiparasitic formulation. The formulations used to treat ectoparasitic infestations, generally, comprise compounds which contribute to irritancy of or toxicity to the animal upon administration thereto. Examples of such compounds include, diazinon and propetamphos, for example. Other compounds, such as pyrethroids and permethrins are suitable for pour-on formulations, whilst in plunge dips it is the organophosphates which are frequently used.

These compounds are toxic not only to the animals but to the administrators alike. Furthermore, many sheep dip formulations cannot be used to treat, for example, larval infestation of wounds such as in the case of the larvae of blowfly which feed on the dead and damaged tissue associated with wounds or scouring. Treatment of blowfly larvae is normally carried out using mild insecticidal creams. Toxic substances, such as contained in many sheep dips, cannot be applied because under no circumstances can the above mentioned formulations be applied to open wounds. The formulations used previously also contribute to are released into the environment. The use of these compounds must therefore be tightly controlled and a considerable number of regulations apply to, for example, disposal of sheep dips.

Accordingly, there exists a need for formulations which when applied to an animal can effectively eradicate common ectoparasitic infestation and any resulting contagious diseases and which formulation similarly alleviates or ameliorates the disadvantages described above whilst minimising trauma and shock to the animal.

Therefore, there is provided by a first aspect of the present invention, an antiparasitic formulation comprising in an antiparasitically effective amount, Eucalyptus oil, Cajeput oil, Lemongrass oil, Clove bud oil, Peppermint oil, Piperonyl and Piperonyl Butoxide. Preferably, the formulation is further diluted with water and in such an embodiment an amount of a suitable surfactant is also included in the formulation in addition to lanolin.

In a preferred embodiment, the formulation comprises:

|  | % By Volume |
| --- | --- |
| Eucalyptus oil | 4–6 |
| Cajeput oil | 0.5–2.5 |
| Lemongrass oil | 1–3 |
| Clove bud oil | 1.5–3.5 |
| Peppermint oil | 0.5–2.5 |
| Piperonyl | 1.5–3.5 |
| Piperonyl Butoxide | 0.3–0.9 |
| Surfactant | 0.05–0.15 |
| Lanolin | 0.5–1.5 |
| Water | 80–90% |

Preferably, however, the formulation comprises in approximate amounts by volume, 5.3% Eucalyptus oil, 1.3% Cajeput oil, 2.0% Lemongrass oil, 2.5% Clove bud oil, 1.3% Peppermint oil, 2.7% piperonyl, 0.6% Piperonyl Butoxide, Surfactant 0.1%, lanolin 1% and water 83.20%.

In a preferred embodiment the formulation may be further diluted to 1 part formulation per 200 parts water, for use as a sheep dip.

The formulations according to the invention are particularly advantageous because they avoid the use of hazardous compounds such as organophosphates which can be toxic both to the animal the uses and the environment. The absence of such compounds also minimises any trauma, shock or irritancy to the animal. The formulations are also safe for use by humans without risk to health and they are also considerably less damaging to the environment. The oils used are registered with the Department of Novel Foods and Flavours at the Ministry of Agriculture Fisheries and Foods. Neither the Council of Europe's Committee of Experts on Flavouring Substances nor any other European committee has recommended limits on the use of these essential oils. These oils have been evaluated by the US Flavouring Extract Manufacturers' Association (FEMA) who have classified them as GRAS (Generally Recognised As Safe) in 1965. These assessments were published in a paper Hall R. L. and Oser B. L. (1965). The formulations of the present invention therefore avoid the use of any organophosphates, permethrins, pyrethrums or derivatives thereof so they are significantly safer for the animal, the operator and the environment, In another aspect of the invention, the formulation according to the invention may, advantageously, be used in the treatment of an animal body so as to, for example, treat ectoparasitic infestation, such as, in sheep, and also any subsequent contagious diseases resulting from the infestation.

According to a further aspect of the invention, there is also provided use of a formulation according to the invention for the manufacture of a medicament for treating an animal of ectoparasitic infestation. The formulations may be applied directly to the animal but preferably are used in a total immersion dip, such as used in a sheep dip, thus allowing the formulation to sufficiently penetrate the fleece so as to substantially eradicate the infestation.

External parasites of sheep include, amongst others, *Damalinia ovis* (biting louse), *Linognathus ovillus* (sucking louse), Lucilia spp (blowfly), Culicoides (midges), *Hydrotaea irritans* (headfly). The formulation of the invention may be used to control infestation of sheep by these parasites.

Other parasites that may be effectively eradicated by the formulation of the invention include scab mite (Psoroptes Communia Ovis), tick pyremia and other tick borne fever, sarcoptic mange and keds. The formulation of the invention is, however, particularly useful in repelling the blowfly parasite and in eradicating the larvae of the blowfly which infest open wounds in sheep or areas where scouring occurs. Thus, the formulation is particularly advantageous by virtue of its use as a dip formulation and yet which is sufficiently non-toxic to the animal that it can also be used, not only to repel the blowfly but to eradicate blowfly larvae, which cannot normally be treated with sheep dip formulations.

As is known, oil of eucalyptus is obtained from various species of eucalyptus and the resulting oils do not possess a uniform analysis. It is believed, however, that the properties of the eucalyptus oil according to the invention are not dependent on a particular source of oil of eucalyptus and one may use oil derived from *Eucalyptus globulus* and/or *Eucalyptus dives*. Eucalyptus oil is rich in cineole and desirably eucalyptus oil according to the invention comprises cineole and preferably 1–8 cineole in an amount of from approximately 35 to 90% by volume.

The invention may be more clearly described by reference to the following example:

A formulation according to the invention was prepared by combining and mixing all of the oils of the following ingredients in the approximate amounts provided:

|  | % product |
| --- | --- |
| Eucalyptus oil | 5.3 |
| Cajeput oil | 1.3 |
| Lemongrass oil | 2.0 |
| Clove bud oil | 2.5 |
| Peppermint oil | 1.3 |
| Piperonyl | 2.7 |
| Piperonyl Butoxide | 0.6 |
| Surfacare T20 | 0.1 |
| Lanolin | 1% |
| Water | 83.20 |
| Total | 100% |

The essential oils together with piperonyl and piperonyl butoxide are mixed. The mixture is then slowly stirred at ambient temperature and then the surfactant is added in addition to a small amount of water and lanolin. The mixture is then high shear stirred to a cream consistency before the final addition of water up to the percentage amount identified above. The product is then pH tested and sampled against a GC standard. Application of the formulation to sheep by way of a plunge dip served to alleviate infestation of sheep by their common parasites.

EXAMPLE

A number of field trials were conducted to evaluate the effectiveness of the above composition in treating ectoparasitic infection of sheep. A solution of the composition further diluted to 1 part composition to 200 parts water was prepared for application by way of a plunge dip. The dipping tank held approximately 400 gallons. 1000 animals were passed through the dipping tank. Each animal absorbed approximately 1.5 liters of solution in the fleece. After each 75 lamb/ewe dip the dipping tank was further topped up with the same solution to make up 400 gallons. After this field trial on Jul. 2, 1999, all animals were protected from blowfly and other ectoparasitic infestations until September when a further dip was performed. The period between July and September is the most crucial as at least 70 out of every 1000 animals suffer blowfly strike during this period.

In further tests, the formulation of the invention was applied directly to healthy live specimens of ticks, blowfly and their maggots, headfly, the mite psoroptes communia ovis that causes sheep scab, redmite, and both types of lice the formula of the invention induced 100% death of all these parasites in less than one minute.

What is claimed is:

1. An antiparasitic formulation comprising by volume, Eucalyptus oil 4–6%, Cajeput oil 0.5–2.5%, Lemongrass oil 1–3%, Clove bud oil 1.5%–3.5%, peppermint oil 0.5–2.5, Piperonyl 1.5–3.5%, Piperonyl Butoxide 0.3–0.9%, Surfactant 0.05–0.15%, 0.5–1.5% lanolin and Water 80–90%.

2. A formulation according to claim 1 comprising in amounts by volume, Eucalyptus oil 5.3%, Cajeput oil 1.3, Lemongrass oil 2.0%, Clove bud oil 2.5%, Peppermint oil 1.3%, Piperonyl 2.7%, Piperonyl Butoxide 0.6%, Surfactant 0.1%, lanolin 1% and Water 83.20%.

3. A formulation according to claim 1 which is further diluted to 1 part formulation to 200 parts water.

4. A formulation according to claim 1 for use in the treatment of an ectoparasite in an animal.

5. A formulation according to claim 4 wherein said animal is a sheep.

6. A formulation according to claim 4 wherein said ectoparasite is blowfly or its larvae.

7. A sheep dip comprising a formulation according to claim 1.

8. A method for treating ectoparasitic infestation of an animal or for repelling said parasites which comprises applying the formulation of claim 1 to the animal.

9. A method for treating ectoparasitic infestation of an animal or for repelling said parasites which comprises applying the formulation of claim 2 to the animal.

10. A method according to claim 8 wherein the animal is sheep.

11. A method according to claim 9 wherein the animal is sheep.

* * * * *